US005962754A

United States Patent [19]
Robin et al.

[11] Patent Number: 5,962,754
[45] Date of Patent: Oct. 5, 1999

[54] METHOD FOR THE PREPARATION OF 3-BROMO-1,1,1-TRIFLUOROPROPANE

[75] Inventors: Mark L. Robin, West Lafayette, Ind.; John Cheng-Ping Qian; Thomas F. Rowland, both of El Dorado, Ark.; Robin Michael Palculict, Junction City, Ark.

[73] Assignee: Great Lakes Chemical Corporation, West Lafayette, Ind.

[21] Appl. No.: 09/167,947

[22] Filed: Oct. 7, 1998

[51] Int. Cl.[6] .................................................... C07C 19/07
[52] U.S. Cl. ............................................................. 570/174
[58] Field of Search ..................................... 570/174, 175

[56] References Cited

U.S. PATENT DOCUMENTS

| 2,644,845 | 7/1953 | McBee . |
| 2,787,646 | 4/1957 | Haszeldine . |

FOREIGN PATENT DOCUMENTS

| 63156742 A2 | 6/1988 | Japan . |
| 63156797 A2 | 6/1988 | Japan . |

OTHER PUBLICATIONS

Speierr, J.L., et al., "Relative consecutive–competitive rate constants in the synthesis of organoalkoxysilanes using molten sodium" *Organometallics* (1991), 10(9), 3046–9 (Abstract only attached).

Horn, H.G., et al., "By–products in the synthesis of 3,3,3–trifuoro–1–bromopropane", *Chem.–Ztg.* (1981), 105(4), 123 (Abstract only attached).

Chen, K.S., et al., "Rearrangements and Conformations of Chloroaklyl Radicals by Electron Spin Resonance", *J. Amer. Chem. Soc.*, vol. 96, 2201–8 (1974).

Haszeldine, R.N., et al., "Reactions of fluorocarbon radicals. V. Alternative syntheses for (trifluoromethyl)acetylene (3,3,3–trifluoroporpyne) and the infuluence of polyfluoro groups on adjacent hydrogen and halogen atoms.", *J. Chem. Soc.*, (1951), 2495–504 (Abstract only attached).

Haszeldine, R.N., et al., "The addition of free radicals to unsatuarated systems. II. Radical addition of olefins of the type $RCH:CH_2$.", *J. Chem. Soc.*, (1953), 1199–1206 (Abstract only attached).

Henne, A.L., et al., "Influence of a $CF_3$ Group on an Adjacent Double Bond." *J. Amer. Chem. Soc.*, vol. 72, 3369 (1950).

Henne, A.L., et al., "Influence of a CF3 Group on an Adjacent Double Bond. III. Free Radical Additions", *J. Amer. Chem. Soc.*, vol. 73, 5527–5528 (1951).

*Primary Examiner*—Alan Siegel
*Attorney, Agent, or Firm*—Marshall, O'Toole, Gerstein, Murray & Borun

[57] ABSTRACT

3-bromo-1,1,1-trifluoropropane is produced by reacting 3,3,3-trifluoropropene with hydrogen bromide at elevated temperature, e.g., 150° C. to 800° C., in the presence of an active carbon catalyst. The conversion, yield and selectivity are unexpectedly high.

14 Claims, No Drawings

METHOD FOR THE PREPARATION OF 3-BROMO-1,1,1-TRIFLUOROPROPANE

BACKGROUND OF THE INVENTION

1. Field of the Invention

The present invention relates to a method for the production of 3-bromo-1,1,1-trifluoropropane, and particularly to a method characterized by high conversion, yield and selectivity and using 3,3,3-trifluoropropene as a starting material.

2. Description of the Prior Art

Numerous methods are disclosed in the prior art for the preparation of halogenated alkanes. These methods vary widely, due in part to the different halogens and alkanes involved. The prior art demonstrates that given methods do not readily translate into predictable applications for other compounds. The present invention provides a novel method for the preparation of 3-bromo-1,1,1-trifluoropropane by the addition of anhydrous hydrogen bromide to 3,3,3-trifluoropropene in the presence of an activated carbon catalyst. The reaction is characterized by high selectivity, conversion and yield, and offers significant economic advantages over prior art preparations.

3-Bromo-1,1,1-trifluoropropane is a known chemical, and has found use as a valuable intermediate in the preparation of a variety of useful compounds. For example, 3-bromo-1,1,1-trifluoropropane has been employed in the synthesis of anti-cancer drugs (Japan Kokai Tokyo Koho JP 63156742 and 63156797, 1988; Chemical Abstracts v. 110, 23632 m and v. 109, 190759u), and has also been employed in the synthesis of industrially important phenylalkoxysilanes (e.g., Speierr, et. al, *Organometallics,* 10(9), 3046 (1991).

3-Bromo-1,1,1-trifluoropropane has been prepared in one prior art process via the treatment of 3,3,3-trifluoropropyl methyl ether ($CF_3CH_2CH_2OCH_3$) with HBr (Horn, et. al., *Chem-Ztg,* 105(4), 123, 1981). The starting ether is expensive to produce and, furthermore, the selectivity of the reaction is poor, $CF_3CH_2CH_2OH$ and $(CF_3CH_2CH_2O)_2CH_2$ also being produced.

U.S. Pat. No. 2,787,646 discloses the preparation of 3-bromo-1,1,1-trifluoropropane in low yield via the reaction of 1-bromo-3,3,3-trichloro-propane and antimony V halides. A similar procedure employing 1-bromo-3,3,3-trichloropropane and antimony trifluoride, $SbF_3$, also produced 1-bromo-3,3,3-trifluoro-propane in low yield, as described by Chen, et. al., *J. Amer. Chem. Soc.,* 96, 2201 (1974). Treatment of 1,3-dibromo-1,1-difluoropropane ($BrCF_2CH_2CH_2Br$) with HF in the presence of antimony pentachloride also produced 3-bromo-1,1,1-trifluoropropane in 56% yield.

U.S. Pat. No. 2,644,845 describes the reaction of 1,1,1-trifluoro-propane with bromine to produce 3-bromo-1,1,1-trifluoropropane in 34% yield, along with 2-bromo-1,1,1-trifluoropropane ($CF_3CHBrCH_3$) and 3,3-dibromo-1,1,1-trifluoropropane in yields of 17.6 and 19.0%, respectively.

Reaction of 3-iodo-1,1,1-trifluoropropane ($CF_3CH_2CH_2I$) with bromine has been reported to produce 3-bromo-1,1,1-trifluoropropane, 3,3-dibrom-1,1,1-trifluoropropane and 3-bromo-1,1,1-trifluoro-3-iodopropane in yields of 13%, 26%, and 14%, respectively (*J. Chem. Soc.,* 1951, 2495). Treatment of 3-iodo-1,1,1-trifluoropropane with bromine under ultraviolet irradiation also is known to produce 3-bromo-1,1,1-trifluoropropane (*J. Chem. Soc.,* 1953, 1199).

Henne, et. al., *J. Amer. Chem. Soc.,* 72, 3369 (1950), teaches that due to the powerful electronegative effect of the $CF_3$ group, the addition of hydrogen halides to 3,3,3-trifluoropropene is difficult. Hence, this addition has been accomplished in the past only via the use of ultraviolet light or powerful Lewis acid catalysts such as aluminum tribromide. For example, Henne, *op. cit.,* describes the reaction of 3,3,3-trifluoropropene and HBr at 100° C. in the presence of $AlBr_3$ to produce 3-bromo-1,1,1-trifluoropropane in 35% yield; the formation of resins in the reaction was also noted. Irradiation of a mixture of 3,3,3-trifluoropropene and hydrogen bromide with a mercury flood lamp for 24 hours in a quartz tube also has been reported to produce 3-bromo-1,1,1-trifluoropropane, for example see Henne, et. al., *J. Amer. Chem. Soc.,* 73, 5527 (1951).

Although the above described methods produce 3-bromo-1,1,1-trifluoropropane, these prior art methods are characterized by numerous disadvantages, including expensive raw materials, poor yields and poor selectivity which preclude their use on a commercial scale.

SUMMARY OF THE INVENTION

In brief, the present invention is directed to a method for the production of 3-bromo-1,1,1-trifluoropropane by reacting 3,3,3-trifluoro-propene and hydrogen bromide at elevated temperature in the presence of active carbon, and thereafter recovering the resulting 3-bromo-1,1,1-trifluoropropane from the reaction mixture.

It is an object of the present invention to provide a method for the production of 3-bromo-1,1,1-trifluoropropane from readily available starting materials.

A further object of this invention is to provide a method for the production of 3-bromo-1,1,1-trifluoropropane which has high conversion, yield and selectively for the desired product.

It is another object of the present invention to provide a method for the production of 3-bromo-1,1,1-trifluoropropane, as described, which does not produce significant amounts of undesirable by-products.

Further objects and advantages of the present invention will be apparent from the description of the preferred embodiment which follows.

DESCRIPTION OF THE PREFERRED EMBODIMENT

For the purposes of promoting an understanding of the principles of the invention, reference will now be made to the preferred embodiment and specific language will be used to describe the same. It will nevertheless be understood that no limitation of the scope of the invention is thereby intended, such further modifications in the invention, and such further applications of the principles of the invention being contemplated as would normally occur to one skilled in the art to which the invention relates.

The present invention is based upon the discovery that 3-bromo-1,1,1-trifluoropropane may be produced via the reaction of 3,3,3-trifluoropropene and anhydrous (gaseous) hydrogen bromide at elevated temperatures in the presence of an active carbon catalyst. The conversion and selectivity for this process are unexpectedly high, rendering the process applicable to commercial scale production.

The basic method of the present invention involves the reaction of 3,3,3-trifluoropropene and gaseous hydrogen bromide in the presence of active carbon according to the following reaction (I)

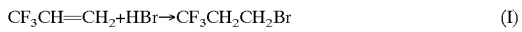

$$CF_3CH{=}CH_2 + HBr \rightarrow CF_3CH_2CH_2Br \qquad (I)$$

The reaction (I) is carried out by contacting 3,3,3-trifluoropropene and HBr at elevated temperatures in the presence of active carbon. Although preferred ranges for contact times and molar ratios are stated hereafter, these ranges are not critical. In addition, the reaction may be carried out at ambient or elevated pressures.

The temperature of the reaction is generally one which is high enough to provide a desired amount and rate of conversion of the 3,3,3-tri-fluoropropene, and low enough to avoid deleterious effects such as the production of decomposition products. To achieve the full advantage of the present invention, therefore, the reaction is preferably carried out at a temperature in the range of about 150° C. to about 800° C. A more preferred temperature range for the reaction is in the range of about 200° C. to about 500° C., and especially in the range of about 250° C. to about 450° C. It will be appreciated that the selected temperature for the reaction will depend in part on the contact time employed, in general the desired temperature for the reaction varying inversely with the contact time for the reaction.

The contact time will vary depending primarily upon the extent of conversion desired and the temperature of the reaction. An appropriate contact time, in general, will be inversely related to the temperature of the reaction and directly related to the extent of conversion of 3,3,3-trifluoropropene.

To achieve the full advantage of the present invention, the process of manufacturing 3-bromo-1,1,1-trifluoropropane will be a continuous process that is carried out as a continuous flow of reactants through a heated reaction vessel wherein heating of the reactants may be very rapidly effected. In the continuous process of the present invention, the residence time of the reactants within the reaction vessel is desirably between about 0.1 second and 200.0 seconds, preferably about 0.1 second to about 60.0 seconds, more preferably about 5.0 seconds to about 15.0 seconds, e.g., about 10.0 seconds. An important feature of the method of the present invention is that the reaction is completed within short contact times, thereby reducing the equipment size and cost associated with producing 3-bromo-1,1,1-trifluoropropane. The reactants may be preheated before combining or may be mixed and heated together as they pass through the vessel. Alternatively, the process may be carried out as a batch process with reactant contact time varying accordingly, although the continuous process is preferred. The reaction also can be carried out in a multistage reactor, wherein gradients in temperature, reactant molar ratio, or differences in both reaction temperature and reactant molar ratio may be employed in the reactor stages.

The molar ratio of the reactants may vary widely and is not critical to the inventive method. The preferred ratio of reactants is determined by practical considerations. For example, a molar ratio of HBr to 3,3,3-trifluoro-propene which is extremely low, e.g., 0.01 to 0.5 to 1, will simply require greater recycle of the 3,3,3-trifluoropropene due to the low conversion, whereas a ratio that is very high, e.g., more than 5 to 1, will be wasteful of HBr. A preferred range for the molar ratio of HBr to 3,3,3-trifluoropropene is between about 0.1 and 2.0 to 1, with a ratio of about 1.0 to 1.5 to 1.0 being most preferred.

In accordance with an important feature of the present invention, the reaction of 3,3,3-trifluoropropene with HBr is achieved with new and unexpectedly high conversion, yield and selectively to produce 3-bromo-1,1,1-trifluoropropane by using an activated (active) carbon catalyst. Any commercially available active carbon may be employed, the particular choice depending primarily on economic factors. Either a fixed bed or a fluidized bed of active carbon may be employed within the reactor to achieve the new and unexpectedly high conversions, yields, and selectivities disclosed herein.

The inventive process has several advantageous aspects in addition to those disclosed above. The reaction involves readily obtainable reactants, namely 3,3,3-trifluoropropene and hydrogen bromide, both of which are commercially available. The reaction products are the desired 3-bromo-1,1,1-trifluoropropane ($CF_3CH_2CH_2Br$) and smaller amounts of the 2-bromo-1,1,1-trifluoropropane isomer ($CF_3CHBrCH_3$). The 2-bromo-1,1,1-trifluoropropane isomer is readily separated from the 3-bromo-1,1,1-trifluoropropane product by conventional distillation methods and apparatus and may be treated with a base to regenerate 3,3,3-trifluoropropene for recycle and reaction with HBr. Hence, very high yields of the desired 3-bromo-1,1,1-trifluoropropane product are ultimately achieved. Therefore, the reaction is unexpectedly efficient in its use of the reactants without producing miscellaneous undesirable by-products, and is a highly efficient and advantageous method for the production of 3-bromo-1,1,1-trifluoropropane.

The efficacy of the process of the present invention is illustrated by the following specific examples.

EXAMPLE 1

3,3,3-Trifluoropropene (100 cc/min) and HBr (100 cc/min) were simultaneously fed through a one-half inch by twelve inch 316 stainless steel reactor packed with approximately 9.0 grams of active carbon (Takeda), the reactor being heated to 300° C. in a tube furnace. The reaction products were passed through a scrubber containing dilute aqueous sodium hydroxide to facilitate removal of any acidic reaction product. Analysis of the product stream, via gas chromatography, indicated that the conversion of 3,3,3-tri-fluoropropene was 33%. The selectivity of 3-bromo-1,1,1-trifluoropropane was 85%, and that of the isomer $CF_3CHBrCH_3$ was 6%. Upon recycle of the isomer to the reactor, therefore, the selectivity of 3-bromo-1,1,1-trilluoropropane was 91%.

EXAMPLE 2

The procedure of Example 1 was repeated with various conditions of temperature and contact time (seconds), and the results are summarized in Table 1.

TABLE 1

| TFP cc/min | HBr | Contact Times | Temp | % Conv TFP | % Selectivity 3-BTFP | 2-BTFP | Combined % Select. |
|---|---|---|---|---|---|---|---|
| 91 | 100 | 18 | 100 | 0 | 0 | 0 | 0 |
| 91 | 100 | 6 | 300 | 33 | 85 | 6 | 91 |
| 91 | 100 | 5 | 420 | 44 | 80 | 11 | 91 |
| 45 | 50 | 13 | 300 | 91 | 91 | 6 | 97 |

TFP = 3,3,3-trifluoropropene
3-BTFP = 3-bromo-1,1,1-trifluoropropane
2-BTFP = 2-bromo-1,1,1-trifluoropropane The results in Table 1 also serve to demonstrate the general effects of temperature and contact time on the reaction. Increasing the temperature from 300° C. to 420° C. with a constant contact time of 5 to 6 seconds is seen to result in increased conversion of 3,3,3-trifluoropropene, as would be expected. Increasing the contact time from 6 to 13 seconds at a constant temperature of 300° C. also is seen to result in an increase in the 3,3,3-trifluoropropene conversion. As pointed out previously, the 3,3,3-trifluoropropene conversion is directly related to the temperature and contact time.

EXAMPLE 3

The procedure of Example 1 was repeated, except that the reaction was conducted in the absence of the active carbon catalyst, and the results are summarized in Table 2.

TABLE 2

| TFP cc/min | Contact HBr | Times | Temp | % Conv TFP | % Selectivity 3-BTFP | 2-BTFP | Combined % Select. |
|---|---|---|---|---|---|---|---|
| 91 | 100 | 6 | 300 | 0 | 0 | 0 | 0* |
| 91 | 100 | 5 | 420 | 0 | 0 | 0 | 0* |
| 91 | 100 | 5 | 509 | 0 | 0 | 0 | 0* |

*No carbon
TFP = 3,3,3-trifluoropropene
3-BTFP = 3-bromo-1,1,1-trifluoropropane
2-BTFP = 2-bromo-1,1,1-trifluoropropane The results in Table 2 demonstrate that the reaction fails to proceed in the absence of the active carbon catalyst.

EXAMPLE 4

This example shows that the process of the present invention is readily scaled up to commercial scale and demonstrates the high selectivities attainable via the process. 3,3,3-trifluoropropene (1153 cc/min) and HBr (1352 cc/min) were simultaneously fed through a one inch diameter by two foot long 316 stainless steel reactor packed with active carbon (Takeda) the reactor being heated to 300° C. in a tube furnace. The reaction products were passed through two aqueous scrubbers and the crude product (organic layer) collected and purified by washing with water, drying over $MgSO_4$ and the product subjected to fractional distillation. Analysis of the product stream via gas chromatography indicated that the conversion of 3,3,3-trifluoropropene was 33%. The selectivity of 3-bromo-1,1,1-trifluoropropane was 98%, and the selectivity of the isomer $CF_3CHBrCH_3$ was 1%, for a combined selectivity of 99%.

While the invention has been described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A method for the production of 3-bromo-1,1,1-trifluoropropane which comprises contacting 3,3,3-trifluoropropene with hydrogen bromide in the presence of an active catalyst for a time and at a temperature sufficient to form 3-bromo-1,1,1-trifluoropropane.

2. The method of claim 1, wherein said contacting time is for a period in the range of about 0.1 second to about 200.0 seconds.

3. The method of claim 2, wherein said contacting time is for a period between about 0.1 and 60.0 seconds.

4. The method of claim 1, wherein said temperature is in the range of about 150° C. to about 800° C.

5. The method of claim 4, wherein the temperature is in the range of about 200° C. to about 500° C.

6. The method of claim 5, wherein the temperature is in the range of about 250° C. to about 450° C.

7. The method of claim 1, wherein the molar ratio of hydrogen bromide to 3,3,3-trifluoropropene is in the range of about 0.1–2.5 to 1.

8. The method of claim 1, wherein the molar ratio of hydrogen bromide to 3,3,3-trifluoropropene is at least 0.5 to 1.

9. The method of claim 7, wherein the molar ratio of hydrogen bromide to 3,3,3-trifluoropropene is in the range of about 1–2.5 to 1.

10. The method of claim 1, wherein said 3,3,3-trifluoropropene and hydrogen bromide are reacted in gaseous form in a reactor containing said active carbon catalyst.

11. The method of claim 10, wherein said 3,3,3-trifluoropropene and hydrogen bromide are reacted in gaseous form in a reactor containing a fixed bed of said active carbon catalyst.

12. The method of claim 10, wherein said 3,3,3-trifluoropropene and hydrogen bromide are reacted in gaseous form in a reactor containing a fluidized bed of said active carbon catalyst.

13. The method of claim 10, further comprising the step of separating unreacted 3,3,3-trifluoropropene from the reaction products and recycling the 3,3,3-trifluoropropene to the reactor for reaction with hydrogen bromide.

14. The method of claim 10, further comprising the step of separating a 2-bromo-1,1,1-trifluoropropane isomer from the 3-bromo-1,1,1-trifluoropropane reaction product; contacting the 2-bromo-1,1,1-trifluoro-propene with an alkali to form 3,3,3-trifluoropropene; and reacting said 3,3,3-trifluoropropene with hydrogen bromide in the presence of an active carbon catalyst to form 3-bromo-1,1,1-trifluoropropane.

* * * * *

UNITED STATES PATENT AND TRADEMARK OFFICE
CERTIFICATE OF CORRECTION

PATENT NO. : 5,962,754
DATED : October 5, 1999
INVENTOR(S) : Robin et al.

It is certified that error appears in the above-identified patent and that said Letters Patent is hereby corrected as shown below:

Column 1,
Line 43, "1-bromo-3,3,3-trichloro-propane" should read as
-- 1-bromo-3,3,3-trichloropropane --.
Line 52, "trifluoro-propane" should read as -- trifluoropropane --.

Column 2,
Line 10, "3-bromo-1,1," should read as -- 3-bromo-1,1, --.

Column 3,
Line 7, "3,3,3-tri-fluoropropene" should read as -- 3,3,3-trifluoropropene --.
Line 49, "3,3,3-trifluoro-propene" should read as -- 3,3,3-trifluoropropene --.

Column 4,
Line 33, "tri-fluoropropene" should read as -- trifluoropropene --.

Column 5,
Table 2, Temp column, delete "509" and substitute therefor -- 500 --.

Column 6,
Line 1, after "an active" insert -- carbon --.
Line 41, "trifluoro-propene" should read as -- trifluoropropene --.

Signed and Sealed this

Twenty-second Day of October, 2002

*Attest:*

*Attesting Officer*

JAMES E. ROGAN
*Director of the United States Patent and Trademark Office*